(12) United States Patent
Collyer

(10) Patent No.: US 9,339,416 B2
(45) Date of Patent: May 17, 2016

(54) DRESSINGS

(75) Inventor: Graham John Collyer, Chapel-en-le-frith (GB)

(73) Assignee: Sumed International (UK) Limited, Glossop, Derbyshire (GB)

(*) Notice: Subject to any disclaimer, the term of this patent is extended or adjusted under 35 U.S.C. 154(b) by 812 days.

(21) Appl. No.: 13/575,719

(22) PCT Filed: Jan. 28, 2011

(86) PCT No.: PCT/GB2011/050148
§ 371 (c)(1),
(2), (4) Date: Sep. 27, 2012

(87) PCT Pub. No.: WO2011/092512
PCT Pub. Date: Aug. 4, 2011

(65) Prior Publication Data
US 2013/0012897 A1   Jan. 10, 2013

(30) Foreign Application Priority Data
Jan. 29, 2010 (GB) .................................. 1001466.0

(51) Int. Cl.
*A61M 27/00* (2006.01)
*A61M 1/00* (2006.01)
*A61F 13/00* (2006.01)
*A61F 13/02* (2006.01)

(52) U.S. Cl.
CPC ....... *A61F 13/0203* (2013.01); *A61F 13/00068* (2013.01); *A61F 13/00085* (2013.01); *A61F 2013/00089* (2013.01); *A61F 2013/00165* (2013.01); *A61F 2013/00289* (2013.01)

(58) Field of Classification Search
CPC .................. A61F 13/0068; A61F 2013/00089; A61F 13/0085; A61F 2013/00289
USPC .......................................... 604/543, 319, 304
See application file for complete search history.

(56) References Cited

U.S. PATENT DOCUMENTS

| 2,068,703 A | 1/1937 | Powdermaker |
| 4,655,209 A | 4/1987 | Scott |

(Continued)

FOREIGN PATENT DOCUMENTS

| JP | 2009095476 A | 5/2009 |
| WO | 02015816 A2 | 2/2002 |

(Continued)

OTHER PUBLICATIONS

Patent Cooperation Treaty, PCT Notification of Transmittal of the International Search Report and the Written Opinion of the International Searching Authority, or the Declaration for Application No. PCT/GB2011/050148 dated Jul. 7, 2011, 12 pages.

(Continued)

*Primary Examiner* — Jacqueline Stephens
(74) *Attorney, Agent, or Firm* — Hoffman Warnick LLC

(57) ABSTRACT

There is provided a dressing (10) which comprises a cover sheet (20) and an absorbent sheet (30). In one embodiment the cover sheet (20) and absorbent sheet (30) have edges which are coterminous along part of their extent and the cover sheet (20) comprises a portion projecting beyond the edge of the absorbent sheet (30) such that, in use, said portion can overly part of an adjacent dressing. Also provided are methods of using dressings and a kit of parts for forming a patchwork dressing.

18 Claims, 2 Drawing Sheets

(56) References Cited

U.S. PATENT DOCUMENTS

| | | |
|---|---|---|
| 5,158,555 A | 10/1992 | Porzilli |
| 5,160,328 A | 11/1992 | Cartmell et al. |
| 5,423,736 A | 6/1995 | Cartmell et al. |
| 6,018,092 A | 1/2000 | Dunshee |
| 6,362,388 B1 | 3/2002 | Lucas |
| 2005/0256438 A1 | 11/2005 | Lombardozzi |
| 2007/0078367 A1 | 4/2007 | Hilton |

FOREIGN PATENT DOCUMENTS

| | | |
|---|---|---|
| WO | 03092756 A1 | 11/2003 |
| WO | 2007143089 A2 | 12/2007 |

OTHER PUBLICATIONS

Examination Opinion and Search Report for UK Patent Application No. GB1001466.0, dated Apr. 20, 2011, 6 pages.

DRESSINGS

FIELD OF INVENTION

The present invention relates to dressings, particularly though not exclusively to dressings for use on patients with epidermolysis bullosa (EB).

BACKGROUND TO THE INVENTION

Epidermolysis bullosa (EB) is a group of rare genetic skin conditions that cause the skin to blister. EB acquisita is a rare skin condition that causes blistering like other forms of EB but EB acquisita is an autoimmune condition rather than a genetic disease.

The skin of EB sufferers is also fragile and easily damaged. Even slight rubbing can cause the skin to blister and tear. EB sufferers often have open wounds left by the blisters and skin damage which can cause them significant pain and discomfort.

It is known to apply a dressing to affected areas of an EB sufferer's skin to protect a wound against infection and/or further damage and/or to protect intact skin from damage. Known methods of dressing an affected area typically use a number of low-adherent dressing squares which are laid onto the skin or wound next to one another and held in place by a bandage.

The fragile nature of EB sufferer's skin and the fact they can suffer from large areas of skin loss makes the use of dressings difficult and there exists a need for improved dressings. Accordingly, embodiments of the present invention aim to address at least one disadvantage associated with known dressings whether discussed herein or otherwise.

SUMMARY OF INVENTION

According to a first aspect of the present invention there is provided a dressing comprising a cover sheet and an absorbent sheet, wherein the cover sheet and absorbent sheet have edges which are coterminous along part of their extent and wherein the cover sheet comprises a portion projecting beyond the edge of the absorbent sheet such that, in use, said portion can overly part of an adjacent dressing.

Suitably, the absorbent sheet is arranged to absorb water. The absorbent sheet may be arranged to absorb and adsorb water. Alternatively, the absorbent sheet may be arranged to adsorb water but may absorb little or no water. Unless otherwise stated references hereafter to an absorbent sheet should be taken to mean a sheet which is arranged to absorb and/or adsorb water.

Suitably, the cover sheet projects beyond the edge of the absorbent sheet in at least one direction. Suitably, the cover sheet is larger than the absorbent sheet such that it projects beyond the edge of the absorbent sheet in at least one direction. Suitably, the cover sheet projects beyond the edge of the absorbent sheet in only one direction. Alternatively, the cover sheet may project beyond the edge of the absorbent sheet in two directions.

Suitably, the portion of the cover sheet which projects beyond the edge of the absorbent sheet is adapted such that, in use, it can be adhered to an adjacent dressing. Suitably, the portion of the cover sheet which projects beyond the edge of the absorbent sheet is adapted to be adhered over the cover sheet of an adjacent dressing, in use. Suitably, in use, adjacent dressings may be adhered to one another using the portion of the cover sheet which projects beyond the edge of the absorbent sheet such that said adjacent dressings can be secured in position relative to one another.

Suitably, the portion of the cover sheet which projects beyond the edge of the absorbent sheet carries an adhesive such that, in use, it can be adhered to an adjacent dressing.

Suitably, the dressing is adapted such that, in use, it can be positioned: (i) next to a like dressing such that the portion of the cover sheet which projects beyond the edge of the absorbent sheet overlies said like dressing; and/or (ii) next to a like dressing such that a portion of a cover sheet of said like dressing which projects beyond the edge of an absorbent sheet of said like dressing overlies the dressing.

Suitably, the dressing is adapted such that it can abut against an adjacent dressing in use. Suitably, the absorbent sheet is adapted such that, in use, it can abut an absorbent sheet of an adjacent dressing.

Suitably, the dressing comprises an absorbent sheet having a first edge which a portion of the cover sheet projects beyond and wherein a second opposed edge of the absorbent material is adapted to mate with a first edge of an absorbent sheet of a like dressing such that the absorbent sheets of like dressings contact one another. Suitably, the dressing comprises an absorbent sheet having a first edge which a portion of the cover sheet projects beyond and wherein a second opposed edge of the absorbent material is adapted to mate with a first edge of an absorbent sheet of a like dressing such that the absorbent sheets of like dressings abut one another.

Suitably, the dressing comprises a rectilinear form. Suitably, the absorbent sheet comprises a rectilinear form. Suitably, the cover sheet comprises a rectilinear form. Suitably, the absorbent sheet is rectangular. The absorbent sheet may be square. Suitably, the cover sheet is rectangular. The cover sheet may be square.

Suitably, the absorbent sheet is substantially rectangular and its edge has four sides.

Suitably, the cover sheet edge is coterminous with the absorbent sheet edge along three of its sides and a portion of the cover sheet projects beyond the edge of the absorbent sheet on one of its sides. Suitably therefore, in use, the projecting portion may be used to attach the dressing to one adjacent dressing on the side of the projecting portion. Suitably, the cover sheet edge is coterminous with the absorbent sheet edge along the length of three of its sides and a portion of the cover sheet projects beyond the edge of the absorbent sheet along the length of one of its sides. Suitably, the cover sheet is substantially rectangular. Suitably, the cover sheet fully covers a face of the absorbent sheet. Suitably, the portion of the cover sheet which extends beyond the edge of the absorbent sheet is rectangular.

Alternatively, the cover sheet edge may be coterminous with the absorbent sheet edge along two of its sides and a portion of the cover sheet may project beyond the edge of the absorbent sheet on two of its sides. Suitably therefore, in use, the projecting portion may be used to attach the dressing to two adjacent dressings, one on each of the sides of the projecting portion. The cover sheet edge may be coterminous with the absorbent sheet edge along the length of two of its sides and a portion of the cover sheet may project beyond the edge of the absorbent sheet along the length of two of its sides. Suitably, the cover sheet is substantially rectangular. Suitably, the cover sheet fully covers a face of the absorbent sheet. Suitably, the portion of the cover sheet which extends beyond the edge of the absorbent sheet is generally "L" shaped.

Suitably, the absorbent sheet comprises foam. Suitably, the absorbent sheet comprises polyurethane. Suitably, the absorbent sheet comprises polyurethane foam. Suitably, the absorbent sheet comprises a hydrophilic material. Suitably, the absorbent sheet comprises a hydrophilic polyurethane foam.

Suitably, the absorbent sheet consists of foam. Suitably, the absorbent sheet consists of polyurethane. Suitably, the absorbent sheet consists of polyurethane foam. Suitably, the absorbent sheet consists of a hydrophilic material. Suitably, the absorbent sheet consists of a hydrophilic polyurethane foam.

Suitably, the absorbent sheet is permeable to air and to water vapour. Suitably, the absorbent sheet is permeable to liquid water. Suitably, the absorbent sheet is permeable to liquids.

Suitably, the absorbent sheet is adapted to absorb exudate from a wound. The absorbent sheet may be able to absorb between 1 and 1000 times its own weight in water.

Suitably, the absorbent sheet has a thickness of between 2 mm and 10 mm, for example between 3 mm and 7 mm, for example around 4 mm or around 5 mm.

Suitably, the absorbent sheet has a width of between 5 cm and 20 cm, for example around 10 cm. Suitably, the absorbent sheet has a length of between 5 cm and 20 cm, for example around 10 cm.

Suitably, the cover sheet comprises a film. Suitably, the cover sheet comprises polyurethane. Suitably, the cover sheet comprises a polyurethane film. Suitably, the cover sheet is vapour permeable. Suitably, the cover sheet comprises a vapour permeable film. Suitably, the cover sheet comprises vapour permeable polyurethane film.

Suitably, the cover sheet has a thickness of 1 mm or less, for example of 0.5 mm or less, for example around 0.1 mm or around 0.2 mm.

Suitably, the cover sheet is permeable to air and to water vapour. Suitably, the cover sheet comprises a film which is permeable to air and to water vapour. Suitably, the cover sheet is impermeable to liquids. Suitably, the cover sheet is impermeable to micro-organisms.

Suitably, in use, the cover sheet provides a barrier to micro-organisms. Suitably, the cover sheet provides a barrier to micro-organisms such that, in use, it prevents or minimises the ingress of infection through the fluid pathway which is formed in the dressing as the foam becomes saturated with fluid.

Suitably, in use, the portion of the cover sheet which extends beyond the edge of the absorbent sheet can be overlapped with and adhered to an adjacent dressing such that the overlapping cover sheet portion forms a junction of the dressings which is impermeable to liquids. Suitably, in use, the portion of the cover sheet which extends beyond the edge of the absorbent sheet can be overlapped with and adhered to an adjacent dressing such that the overlapping cover sheet portion forms a junction of the dressings which is impermeable to micro-organisms.

Suitably, the cover sheet and absorbent sheet are adhered to one another. Suitably, the cover sheet is adhered to the absorbent sheet using an acrylic adhesive. Alternatively, or in addition the cover sheet may be adhered to the absorbent sheet using one or more of a zinc oxide based adhesive, a polyurethane based adhesive and a silicone adhesive.

Suitably, the absorbent sheet comprises a first face adapted to face a patient's skin and/or wound in use. Suitably, the absorbent sheet comprises a first face adapted to contact skin and/or a wound in use.

Suitably, the dressing comprises an adhesive adapted to contact skin and/or a wound over which the dressing is applied in use. Suitably, the dressing comprises a low-adherent adhesive adapted to contact skin and/or a wound over which the dressing is applied in use. Suitably, the dressing comprises a silicone adhesive adapted to contact skin and/or a wound over which the dressing is applied in use.

Suitably, the dressing comprises an adhesive on a first face of the absorbent sheet. Suitably, the dressing comprises a low-adherent adhesive on a first face of the absorbent sheet. Suitably, the dressing comprises a silicone adhesive on a first face of the absorbent sheet. Suitably, the dressing comprises a soft silicone adhesive on a first face of the absorbent sheet.

Suitably, the dressing comprises a discontinuous adhesive layer on a first face of the absorbent sheet. Suitably, the dressing comprises a low-adherent adhesive layer which is discontinuous. Suitably, the dressing comprises a silicone adhesive layer which is discontinuous.

Suitably, the dressing comprises an adhesive layer on a first face of the absorbent sheet and said layer is discontinuous such that, in use, exudate can enter into the absorbent sheet via said discontinuities.

Suitably, the adhesive on the first face of the absorbent sheet comprises a series of spaced apart units, preferably lines of adhesive. Suitably, spaces between the adhesive provide a pathway for fluid to enter into the absorbent sheet. Suitably, the lines of adhesive extend between two edges of the absorbent sheet and run substantially perpendicular to said edges. Suitably, the lines of adhesive extend between two edges of the absorbent sheet and run at an oblique angle to said edges Suitably, the lines of adhesive have a width of between 1 mm and 5 mm, for example around 2 mm or around 3 mm. Suitably the gaps between the lines of adhesive have a width of between 1 mm and 10 mm, for example around 3 mm or around 4 mm.

Alternatively, the adhesive on the first face of the absorbent sheet may comprise a mesh or net pattern of adhesive. The adhesive on the first face of the absorbent sheet may for example comprise a layer of adhesive having a series of circular apertures therein to form a mesh of adhesive on the absorbent sheet. The adhesive on the first face of the absorbent sheet may for example comprise a layer of adhesive having a series of elliptical apertures therein to form a mesh of adhesive on the absorbent sheet. The adhesive on the first face of the absorbent sheet may for example comprise a layer of adhesive having a series of rectilinear apertures therein to form a mesh of adhesive on the absorbent sheet.

Suitably, the dressing comprises an adhesive interposing a second face of the absorbent sheet and the cover sheet. Suitably, the dressing comprises an adhesive layer interposing a second face of the absorbent sheet and the cover sheet and which adhesive layer may be continuous or discontinuous.

Suitably, the dressing comprises a first adhesive on a first face of the absorbent sheet for releasably adhering the dressing to a patient. Suitably, the dressing comprises a second adhesive for non-releasably adhering the cover sheet to the absorbent sheet. Suitably, the dressing comprises both first and second adhesives.

Suitably, the dressing comprises a second adhesive on the face of the cover sheet which faces the absorbent sheet. Suitably, the dressing comprises a second adhesive interposing a second face of the absorbent sheet and the cover sheet such that the cover sheet and absorbent sheet are bonded to one another by the second adhesive. Suitably, the portion of the cover sheet which projects beyond the edge of the absorbent sheet also carries said second adhesive.

Suitably, the first adhesive comprises a low-adherent adhesive. Suitably, the first adhesive comprises a silicone adhesive. Suitably, the first adhesive comprises a soft silicone adhesive. Suitably, the first adhesive consists of a low-adherent adhesive. Suitably, the first adhesive consists of a silicone adhesive. Suitably, the first adhesive consists of a soft silicone adhesive.

Suitably, the second adhesive comprises an acrylic adhesive. Suitably, the second adhesive consists of an acrylic adhesive. The second adhesive may comprise a zinc oxide based adhesive. The second adhesive may comprise a polyurethane based adhesive. The second adhesive may comprise a silicone adhesive.

Suitably, in use, if the dressing is not to be applied to a patient such that the portion of the cover sheet which extends beyond the edge of the absorbent material overlaps with an adjacent dressing then said portion can be cut off to ensure it does not become stuck to the patient's skin. Alternatively, the portion of the cover sheet which extends beyond the edge of the absorbent material may be adhered to a patient's skin, in use, if the patient's skin is robust enough to allow the portion to be subsequently peeled from the skin when the dressing is removed.

Suitably, the dressing is provided with a release sheet. Suitably, the dressing is provided with a release sheet which is releasably adhered to a first face of the absorbent sheet. Suitably, in use, the release sheet can be peeled away from the absorbent sheet to expose an adhesive carried by the first face of the absorbent sheet and allow the dressing to be applied to a patient.

Suitably, the dressing is provided with a release sheet which is releasably adhered to the portion of the cover sheet which extends beyond the edge of the absorbent material. Suitably, in use, the release sheet can be peeled away from said portion of the cover sheet to expose an adhesive carried by the cover sheet and allow said portion of the cover sheet to be adhered over an adjacent dressing.

Suitably, the dressing is provided with a first release sheet which is releasably adhered to a first face of the absorbent sheet. Suitably, the dressing is provided with a second release sheet which is releasably adhered to the portion of the cover sheet which extends beyond the edge of the absorbent material. The dressing may be provided with a release sheet which is releasably adhered to both the absorbent sheet and the cover sheet.

The dressing may comprise a first release sheet which is releasably adhered to a first face of the absorbent sheet and which is also releasably adhered to the portion of the cover sheet which extends beyond the edge of the absorbent material. Alternatively, the dressing may be provided with a first release sheet which is releasably adhered to a first face of the absorbent sheet and a second release sheet which is releasably adhered to the portion of the cover sheet which extends beyond the edge of the absorbent material.

Suitably, a release sheet comprises a flurosilicone covered substrate, for example flurosilicone covered paper, polyester or polyolefin. Suitably, the first release sheet comprises flurosilicone covered paper, polyester or polyolefin.

Suitably, a release sheet comprises a silicone release paper. Suitably, the second release sheet comprises a silicone release paper.

Suitably, the dressing comprises an absorbent sheet, a cover sheet and adhesives. Suitably, the dressing is further provided with a release sheet which is removed in use before application of the dressing to a patient. Suitably, the dressing consists of an absorbent sheet, a cover sheet and adhesives. The dressing may be provided as a dressing product which consists of an absorbent sheet, a cover sheet and adhesives together with a release sheet.

The dressing may be adapted to be a slab dressing. Suitably, a slab dressing is adapted such that it can be laid like a slab adjacent a like dressing such that the absorbent sheets of the dressings abut. The dressing may be adapted to abut an adjacent dressing along at least one edge thereof, preferably along two or more edges thereof. The dressing may be adapted to abut an adjacent dressing for substantially the full thickness of the dressing along at least one edge thereof, preferably along two or more edges thereof. Suitably, the absorbent sheet has one or more edges whose surface plane extends substantially perpendicular to the first and second faces of said absorbent sheet. Suitably, the edge of the absorbent sheet beyond which the cover sheet projects has a surface plane which extends substantially perpendicular to the first and second faces of said absorbent sheet. Suitably at least one edge of the absorbent sheet, other than the edge beyond which the cover sheet projects, has a surface plane which extends substantially perpendicular to the first and second faces of said absorbent sheet. Suitably, the absorbent sheet has edges whose surface planes each extend substantially perpendicular to the first and second faces of said sheet.

The dressing may be adapted to be a bordered dressing. Suitably, a bordered dressing is adapted such that the cover sheet covers one or more edges of the absorbent sheet. The dressing may comprise one or more bevelled edges, for example one, two or three bevelled edges. The dressing may comprise one or more edges at which the absorbent sheet thins towards the edge such that the cover sheet lies closer to the first side of the absorbent sheet at such an edge than it does towards a central region of the dressing. Suitably, the cover sheet projects beyond a bevelled edge of the absorbent sheet such that it forms a border to the dressing at said edge. The cover sheet suitably projects beyond the bevelled edge by less than 50 mm. The cover sheet suitably projects beyond the bevelled edge by between 5 and 50 mm, preferably around 20 mm or around 10 mm. The dressing may comprise one, two or three such edges. Suitably, the dressing comprises one or more edges at which the absorbent sheet is bevelled and at which the cover sheet contacts the first adhesive. The dressing may comprise two or three such edges. Suitably, at such edges the cover sheet can be adhered to the skin by the first adhesive in use. The cover sheet may thus from a barrier around edges of the absorbent sheet in use.

In use, a combination of dressings of the type descried in the two paragraphs immediately above may be used to form a patchwork of dressings which collectively form a large dressing having bordered edges and in which the cover sheets of adjacent dressings overlap one another.

According to a second aspect of the present invention there is provided a dressing comprising a cover sheet and an absorbent sheet, wherein the dressing is adapted such that, in use, the dressing can be positioned adjacent a like dressing such that the absorbent sheet of the dressing abuts the absorbent sheet of the like dressing and such that a portion of the dressing which projects beyond an edge of the absorbent sheet of the dressing overlies the cover sheet of the like dressing.

The dressing of the second aspect may comprise any feature according to the dressing of the first aspect.

According to a third aspect of the present invention there is provided a method of applying a dressing to a patient, wherein the method comprises applying a first dressing to the patient and then applying a second dressing to a patient such that the second dressing abuts the first and wherein a cover sheet of the second dressing is located to overlap with the first dressing and is adhered thereto to secure the dressings in position relative to one another.

Suitably, the method may further comprise applying one or more further dressings, which may be substantially the same as the second dressing, to a patient.

Suitably, the first dressing comprises a cover sheet and an absorbent sheet. Suitably, the second dressing comprises a cover sheet and an absorbent sheet.

Suitably, the second dressing comprises a cover sheet and an absorbent sheet, wherein the cover sheet and absorbent sheet have edges which are coterminous along part of their extent and wherein the cover sheet comprises a portion projecting beyond the edge of the absorbent sheet and wherein the method comprises locating the dressing such that said portion overlies part of the first dressing.

Suitably, the second dressing comprises a dressing according to the first aspect. The first dressing may comprise a dressing according to the first aspect. If used, the or each further dressing may comprise a dressing according to the first aspect.

The second dressing may comprise a dressing according to the second aspect. The first dressing may comprise a dressing according to the second aspect. If used, the or each further dressing may comprise a dressing according to the second aspect.

The method may comprise applying a dressing to a patient having epidermolysis bullosa.

According to a fourth aspect of the present invention there is provided a method of treating a patient having epidermolysis bullosa, wherein the method comprises applying a dressing according to the first aspect and/or the second aspect to a patient and/or wherein the method comprises applying a dressing according to the method of the third aspect.

According to a fifth aspect of the present invention there is provided a kit of parts for forming a patchwork dressing comprising a patchwork of smaller individual dressings, wherein the kit comprises two or more dressings as described in relation to the first aspect.

Suitably, the kit comprises two or more types of dressing. Each dressing may comprise any feature as described in relation to the first aspect. Suitably, one or more dressings comprises one or more bevelled edges and one or more dressings does not comprises any bevelled edges.

Suitably, the kit comprises a combination of slab and bordered dressings. Suitably, in use slab dressings are laid next to one another in the central area of the patchwork dressing to prevent a fluid path between the individual dressings and bordered dressings are used at the periphery of the patchwork dressing to provide it with a border which is sealed against fluid. The kit may thus be used to form an occlusive patchwork dressing. Suitably said dressing is impermeable to liquid water but not to water vapour.

BRIEF DESCRIPTION OF THE DRAWINGS

For a better understanding of the invention, and to show how embodiments of the same may be carried into effect, reference will now be made, by way of example, to the accompanying diagrammatic drawings in which.

DETAILED DESCRIPTION OF PREFERRED EMBODIMENTS

Figure 1:
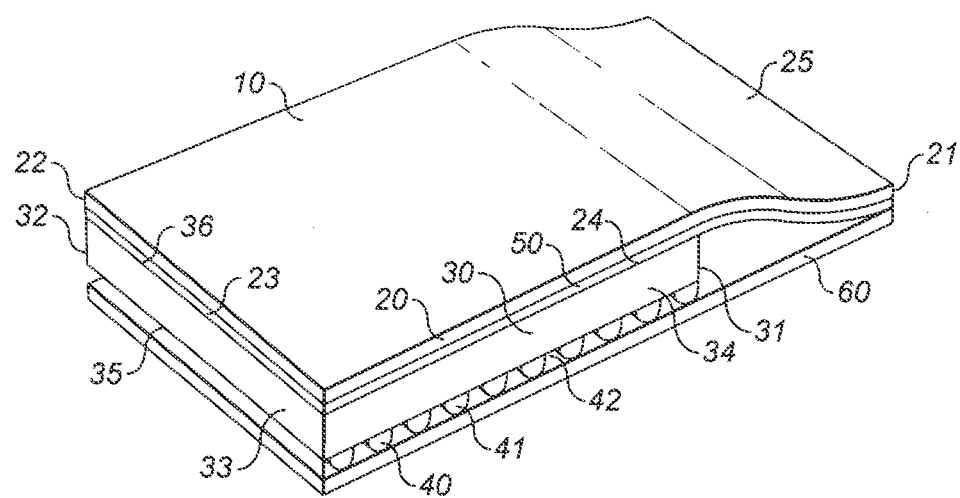
FIG. 1 is a perspective view of a dressing according to an example embodiment of the present invention.
Figure 2:
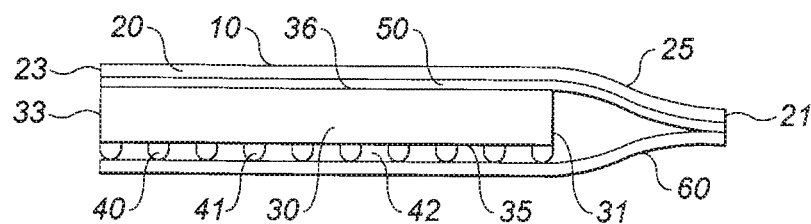
FIG. 2 is a view of a dressing according to an example embodiment of the present invention from a first side.
Figure 3:
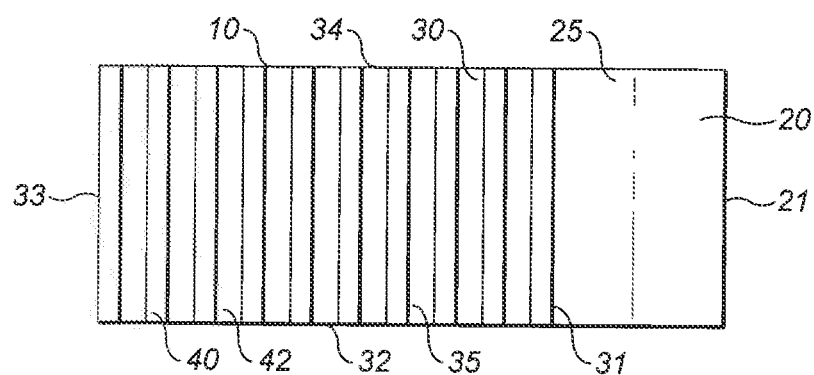
FIG. 3 is an underside view of a dressing according to an example embodiment of the present invention with the release paper removed.

As illustrated by FIGS. 1 to 3 a dressing 10 according to an example embodiment of the present invention comprises a cover sheet 20 and an absorbent sheet 30. In the illustrated embodiment the cover sheet 20 comprises a vapour permeable polyurethane foam and the absorbent sheet 30 comprises a hydrophilic polyurethane foam.

The absorbent sheet comprises a rectangle and has an edge with four sides 31, 32, 33, 34. The cover sheet 20 comprises a rectangle and has an edge with four sides 21, 22, 23, 24.

The edges of the cover sheet 20 and absorbent sheet 30 are coterminous along part of their extent and the cover sheet 20 comprises a portion 25 projecting beyond the edge 31 of the absorbent sheet 30 such that, in use, said portion 25 can overly part of an adjacent dressing. The projecting portion 25 has a rectangular form.

The absorbent sheet 30 carries a first adhesive 40 on a first face 35 thereof and said adhesive 40 is arranged in discrete lines 41 extending between edges 32, 34 of the absorbent sheet. The lines of adhesive 41 are separated by gaps 42 such that the adhesive forms a discontinuous layer on the absorbent sheet 30 such that, in use, fluid may enter the absorbent sheet via the gaps 42. In an alternative embodiment (not shown) the adhesive is applied in a mesh pattern with the mesh comprising circular apertures. In other embodiments (not shown) the mesh may comprise non-circular apertures, and for example may comprise apertures arranged in an irregular fashion. The adhesive is adapted to releasably adhere the dressing to a patient in use and comprises a soft silicone adhesive.

The cover sheet 20 carries an adhesive 50 which interposes the cover sheet 20 and a second face 36 of the absorbent sheet 30 such that the cover sheet 20 and absorbent sheet 30 are adhered to on another. The portion 25 of the cover sheet which projects beyond the edge 31 of the absorbent sheet 30 also carries adhesive 50. The adhesive 50 comprises an acrylic adhesive. The projecting portion 25 of the cover sheet 20 is adapted to be laid over and adhered to an adjacent dressing in use.

The dressing 10 is provided with a release sheet 60 which is releasably adhered to the adhesive 40 carried by the absorbent sheet 30 and to the adhesive 50 carried by the projection portion 25 of the cover sheet 20. In use, the release sheet 60 is peeled away from the dressing 10 to allow the dressing to be applied to a patient and adhered to an adjacent dressing.

Figure 4:
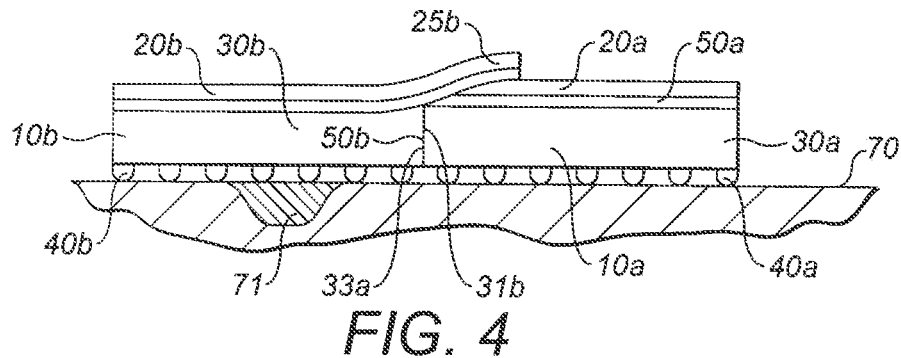
FIG. 4 is a view showing from a first side showing a dressing according to an example embodiment of the present invention in use.

As illustrated by FIG. 4, in use a number of dressings 10a, 10b are applied to the skin 70 and a wound 71 of a patient to form a patchwork dressing.

A first dressing 10a is applied to the skin 70 such that an absorbent sheet 30a and adhesive 40a carried thereby contact the skin 70. The adhesive releasably holds the dressing 10a in place such that the dressing can be subsequently removed without damaging the patient's delicate skin. The dressing 10a further comprises a cover sheet 20a which overlies the absorbent sheet 30a and is adhered thereto by adhesive 50a.

The first dressing 10a comprises a dressing of the type 10 described above but which has been modified by cutting off the projecting portion 25 to ensure the acrylic adhesive does not contact the patient's skin. Although acrylic adhesive can be used on skin its tack is often too great to be used on EB patients so if, as in the illustrated example, the projecting portion 25 is not to be used to attach the dressing 10a to an adjacent dressing it is desirable to remove it.

Once the first dressing 10a is located in place a second dressing 10b is located in place. The second dressing 10b is applied to the skin 70 and over a wound 71 such that an absorbent sheet 30b and adhesive 40b carried thereby contact the skin 70. The adhesive releasably holds the dressing 10b in place such that the dressing can be subsequently removed without damaging the patient's delicate skin. The dressing 10b further comprises a cover sheet 20b which overlies the absorbent sheet 30b and is adhered thereto by adhesive 50b.

The second dressing 10b comprises a dressing of the type 10 described above and in this case the dressing has not been modified. The dressing 10b therefore comprises a portion 25a of the cover sheet 20b which projects beyond the edge 31b of the absorbent sheet.

The second dressing 10b is located such that an edge 31b of the absorbent sheet 30b abuts an edge 33a of the absorbent sheet 30a of the first dressing 10a. The projecting portion 25b of the cover sheet 20b of the second dressing 10b is located over a part of the cover sheet 20a of the first dressing and adhered thereto by the acrylic adhesive 50b carried by said projecting portion 25b. The first and second dressings 10a, 10b are thus secured in position relative to one another.

The cover sheets 20a, 20b are substantially impermeable to micro-organisms and thus because the projecting portion 25b of the cover sheet 20b of the second dressing 10b overlaps the cover sheet 20a of the first dressing 10a they cooperate to form a dressing junction which is substantially impermeable to micro-organisms.

If a patchwork dressing is formed exclusively from dressings 10 then the edges of the patchwork dressing are held in place using tape or the like or alternatively the patchwork dressing is held in place by conventional or tubular bandages. Alternatively, central regions of a patchwork dressing can be made using dressings 10 (slab dressings) and the periphery of a patchwork dressing can be made using adapted dressings 110 (bordered dressings) as explained in more detail below with reference to FIG. 5. The bordered dressings each comprise at least one bevelled edge and an extension of the cover sheet so that the cover sheet covers the edge of the absorbent sheet and beyond the absorbent sheet abuts the patient's skin in use to seal the edge of the patchwork dressing against fluid ingress or egress.

Figure 5:
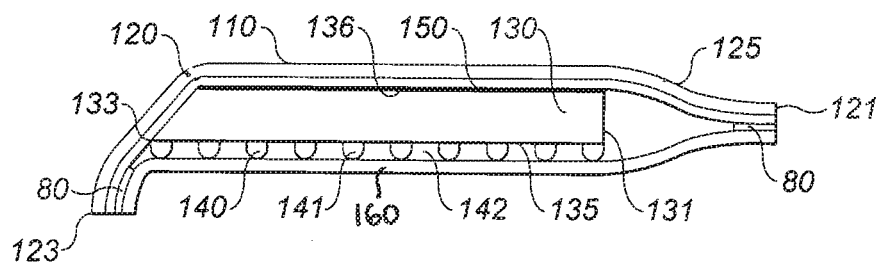
FIG. 5 is a view of a dressing according to another example embodiment of the present invention from a first side.

FIG. 5 illustrates a bordered dressing 110. In this example only one edge is bordered. The dressing 110 comprises a cover sheet 120 and an absorbent sheet 130.

The absorbent sheet comprises a rectangle and has an edge with four sides 131, 132, 133, 134. The cover sheet 120 comprises a rectangle and has an edge with four sides 121, 122, 123, 124.

The edges of the cover sheet 120 and absorbent sheet 130 are coterminous along part of their extent and the cover sheet 120 comprises a portion 125 projecting beyond the edge 131 of the absorbent sheet 130 such that, in use, said portion 125 can overly part of an adjacent dressing. The projecting portion 125 has a rectangular form. The edge 131 of the absorbent sheet has a surface whose plane extends perpendicular to first and second faces of the absorbent sheet 130.

At the edge opposed to the projecting portion 125 the absorbent sheet 130 has a bevelled edge region and the cover sheet 120 extends beyond the edge 133 such that it encloses the absorbent sheet 130, and that its edge 123 forms a portion projecting beyond the absorbent sheet 130 at the edge 133. This portion of the cover sheet 120 is arranged in use to abut the patient's skin in use to seal the edge of the dressing 110 against fluid ingress or egress.

The absorbent sheet 130 carries a first adhesive 140 on a first face 135 thereof and said adhesive 40 is arranged in discrete lines 141 extending between edges 132, 134 of the absorbent sheet. The lines of adhesive 141 are separated by gaps 142 such that the adhesive forms a discontinuous layer on the absorbent sheet 130 such that, in use, fluid may enter the absorbent sheet via the gaps 142. The adhesive is adapted to releasably adhere the dressing to a patient in use and comprises a soft silicone adhesive.

The cover sheet 120 carries an adhesive 150 which interposes the cover sheet 120 and a second face 136 of the absorbent sheet 130 such that the cover sheet 120 and absorbent sheet 130 are adhered to on another. The portion 125 of the cover sheet which projects beyond the edge 131 of the absorbent sheet 30 also carries adhesive 150. The adhesive 150 comprises an acrylic adhesive. The projecting portion 125 of the cover sheet 120 is adapted to be laid over and adhered to an adjacent dressing in use.

The dressing 110 is provided with a release sheet 160 which is releasably adhered to the adhesive 140 carried by the absorbent sheet 130. In one example embodiment the release sheet 160 is conveniently adhered to the adhesive 150 carried by the projection portion 125 of the cover sheet 120 and/or to the portion of the cover sheet 120 arranged in use to abut the patient's skin. In another example embodiment the first adhesive 140 may be used at the projection portion 125 of the cover sheet 120 and/or to the portion of the cover sheet 120 arranged in use to abut the patient's skin to hold the release sheet 160. FIG. 5 shows such an example, with first adhesive 80 arranged between the release sheet and the adhesive 150 on the cover sheet 120. In another particularly preferred embodiment, the adhesive 150 on the cover sheet 120 is used to hold the release sheet 160 with the projection portion 125 of the cover sheet 120, and the first adhesive 140 is used to hold the release sheet 160 with the portion of the cover sheet 120 arranged in use to abut the patient's skin. In use, the release sheet 160 is peeled away from the dressing 110 to allow the dressing to be applied to a patient and adhered to an adjacent dressing.

Figure 6:
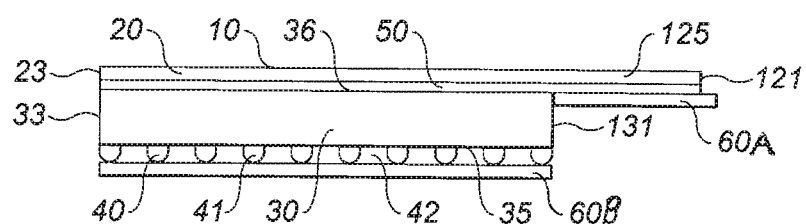
FIG. 6 is a view of a dressing according to yet another example embodiment of the present invention showing an alternative release sheet arrangement.

FIG. 6 shows an alternative embodiment of a release sheet arrangement. The dressing 10 is identical to that of FIGS. 1-3 and is labelled accordingly.

The dressing has a first release sheet 60A which is releasably adhered to the absorbent sheet 30 and which comprises a flurosilicone covered paper and a second release sheet 60B which is releasably adhered to the cover sheet 20 and which comprises a silicone release paper.

It will be appreciated that example embodiments of the present invention may provide a dressing which is convenient to use and which may give beneficial protection against the ingress of infection.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A dressing comprising a cover sheet and an absorbent sheet, wherein the cover sheet and absorbent sheet have edges which are coterminous along part of their extent and wherein the cover sheet comprises a portion projecting beyond the edge of the absorbent sheet such that, in use, said portion can overly part of an adjacent dressing and wherein the cover sheet edge is coterminous with the absorbent sheet edge along three of its sides and a portion of the cover sheet projects beyond the edge of the absorbent sheet on one of its sides.

2. A dressing according to claim 1, wherein the cover sheet is larger than the absorbent sheet such that it projects beyond the edge of the absorbent sheet in at least one direction.

3. A dressing according to claim 1, wherein the cover sheet projects beyond the edge of the absorbent sheet in two directions.

4. A dressing according to claim 1, wherein the portion of the cover sheet which projects beyond the edge of the absorbent sheet is adapted such that, in use, it can be adhered to an adjacent dressing.

5. A dressing according to claim 1, wherein the portion of the cover sheet which projects beyond the edge of the absorbent sheet carries an adhesive such that, in use, it can be adhered to an adjacent dressing.

6. A dressing according to claim 1, wherein the dressing is adapted such that, in use, it can be positioned: (i) next to a like dressing such that the portion of the cover sheet which projects beyond the edge of the absorbent sheet overlies said like dressing; and/or (ii) next to a like dressing such that a portion of a cover sheet of said like dressing which projects beyond the edge of an absorbent sheet of said like dressing overlies the dressing.

7. A dressing according to claim 1, wherein the absorbent sheet is adapted such that, in use, it can abut an absorbent sheet of an adjacent dressing.

8. A dressing according to claim 1, wherein sheet edge is coterminous with the absorbent sheet edge along the length of three of its sides and a portion of the cover sheet projects beyond the edge of the absorbent sheet along the length of one of its sides.

9. A dressing according to claim 1, wherein the absorbent sheet has at least one of the following: a thickness of between 2 mm and 10 mm or a width of between 5 cm and 20 cm and a length between 5 cm and 20 cm.

10. A dressing according to claim 1, wherein the cover sheet provides a barrier to micro-organisms such that, in use, it prevents or minimises the ingress of infection through the fluid pathway which is formed in the dressing as the foam becomes saturated with fluid.

11. A dressing according to claim 1, wherein the portion of the cover sheet which extends beyond the edge of the absorbent sheet can be overlapped with and adhered to an adjacent dressing such that the overlapping cover sheet portion forms a junction of the dressings which is impermeable to at least one of the following: liquids or micro-organisms.

12. A dressing according to claim 1, wherein the dressing comprises an adhesive adapted to contact skin and/or a wound over which the dressing is applied in use.

13. A dressing according to claim 1, wherein the dressing comprises a first adhesive on a first face of the absorbent sheet for releasably adhering the dressing to a patient and wherein the dressing comprises a second adhesive for non-releasably adhering the cover sheet to the absorbent sheet.

14. A kit of parts for forming a patchwork dressing comprising a patchwork of smaller individual dressings, wherein the kit comprises two or more dressings comprising:
a cover sheet; and
an absorbent sheet,
wherein the cover sheet and absorbent sheet have edges which are coterminous along part of their extent and wherein the cover sheet comprises a portion projecting beyond the edge of the absorbent sheet such that, in use, said portion can overly part of an adjacent dressing and wherein the cover sheet edge is coterminous with the absorbent sheet edge along three of its sides and a portion of the cover sheet projects beyond the edge of the absorbent sheet on one of its sides.

15. A kit according to claim 14, wherein the kit comprises a combination of slab and bordered dressings.

16. A kit according to claim 15, wherein the slab dressings are laid next to one another in the central area of the patchwork dressing to prevent a fluid path between the individual dressings and bordered dressings are used at the periphery of the patchwork dressing to provide it with a border which is sealed against fluid.

17. A dressing comprising a cover sheet and an absorbent sheet, wherein the cover sheet and absorbent sheet have edges which are coterminous along part of their extent and wherein the cover sheet comprises a generally "L" shaped portion projecting beyond the edge of the absorbent sheet such that, in use, said portion can overly part of an adjacent dressing and the cover sheet projects beyond the edge of the absorbent sheet in only one direction.

18. A dressing comprising a cover sheet and an absorbent sheet, wherein the cover sheet and absorbent sheet have edges which are coterminous along part of their extent and wherein the cover sheet comprises a portion projecting beyond the edge of the absorbent sheet such that, in use, said portion can overly part of an adjacent dressing and the absorbent sheet includes at least one of the following: foam or polyurethane.

* * * * *